United States Patent
Beeckler et al.

(10) Patent No.: US 12,263,013 B2
(45) Date of Patent: Apr. 1, 2025

(54) CAGE DEFORMATION MODELING

(71) Applicant: Biosense Webster (Israel) Ltd., Yokneam (IL)

(72) Inventors: Christopher Thomas Beeckler, Brea, CA (US); Justin George Lichter, Irvine, CA (US); Joseph Thomas Keyes, Sierra Madre, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 130 days.

(21) Appl. No.: 18/091,128

(22) Filed: Dec. 29, 2022

(65) Prior Publication Data

US 2024/0215918 A1 Jul. 4, 2024

(51) Int. Cl.
*A61B 5/00* (2006.01)
*A61B 5/06* (2006.01)

(52) U.S. Cl.
CPC ............ *A61B 5/6853* (2013.01); *A61B 5/062* (2013.01); *A61B 5/6885* (2013.01)

(58) Field of Classification Search
CPC ...... A61B 18/1492; A61B 2018/00267; A61B 2090/064; A61B 2090/065; A61B 5/062; A61B 5/287; A61B 5/6853; A61B 5/6858; A61B 5/6859; A61B 5/6885; A61B 5/742; A61B 90/06

See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |

(Continued)

FOREIGN PATENT DOCUMENTS

| | | |
|---|---|---|
| EP | 3537965 A1 | 9/2019 |
| WO | WO 2017/041889 A2 | 3/2017 |
| WO | 2019193545 A1 | 10/2019 |

OTHER PUBLICATIONS

Oesterlein T, Frisch D, Loewe A, Seemann G, Schmitt C, Dössel O, Luik A. Basket-Type Catheters: Diagnostic Pitfalls Caused by Deformation and Limited Coverage. Biomed Res Int. 2016;2016:5340574. doi: 10.1155/2016/5340574. Epub Dec. 13, 2016. PMID: 28070511; PMCID: PMC5187596.

(Continued)

*Primary Examiner* — Amelie R Davis
(74) *Attorney, Agent, or Firm* — Frost Brown Todd LLP

(57) ABSTRACT

Apparatus for medical treatment, consisting of a probe and a processor. The probe has an insertion tube having a distal end configured for insertion into a body cavity of a living subject, and a basket assembly having multiple resilient spines coupled to the distal end of the insertion tube and joined together in a predefined form when the basket assembly is unconstrained by external forces. The probe also has a force sensor configured to output an indication of a force exerted on the basket assembly within the body cavity. The processor is configured to receive the indication of the force, to compute a constrained form of the basket assembly, different from the predefined form, responsively to the force, and to render to a display a graphical image representing the constrained form of the basket assembly.

24 Claims, 6 Drawing Sheets

(56) References Cited

U.S. PATENT DOCUMENTS

| | | |
|---|---|---|
| 6,172,499 B1 | 1/2001 | Ashe et al. |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 6,788,967 B2 | 9/2004 | Haim et al. |
| 6,892,091 B1 | 5/2005 | Haim et al. |
| 7,536,218 B2 | 5/2009 | Govari et al. |
| 7,756,576 B2 | 7/2010 | Levin |
| 7,848,787 B2 | 12/2010 | Osadchy |
| 7,869,865 B2 | 1/2011 | Govari et al. |
| 8,456,182 B2 | 6/2013 | Bar-Tal et al. |
| 8,989,463 B2 | 3/2015 | Barbot et al. |
| 9,272,132 B2 | 3/2016 | Laufer et al. |
| 9,326,700 B2 | 5/2016 | Govari et al. |
| 10,688,278 B2 | 6/2020 | Beeckler et al. |
| 2014/0228663 A1 | 8/2014 | Kordis et al. |
| 2018/0110979 A1 | 4/2018 | Hiller et al. |
| 2022/0104875 A1 | 4/2022 | Gleiman et al. |
| 2022/0192753 A1 | 6/2022 | Rosenberg |
| 2024/0197393 A1* | 6/2024 | Kingston ............. A61B 5/6859 |

OTHER PUBLICATIONS

EP Search Report dated May 23, 2024, EP Application No. EP 23 21 9663.

* cited by examiner

CAGE DEFORMATION MODELING

FIELD OF THE DISCLOSURE

This disclosure relates generally to imaging, and specifically to presentation of an image of a catheter used in surgery.

BACKGROUND

During a surgical procedure involving inserting a catheter into the vasculature of a patient, it is beneficial to a physician performing the procedure to see a visual image of the catheter within the vasculature. This may be accomplished by tracking the catheter, typically the location of the distal end of the catheter, and presenting on a map of the patient an indication of the location.

If the procedure comprises insertion of the catheter distal end into a chamber of the patient's heart, the presentation typically comprises overlaying the indication, which may comprise an icon of the distal end, on a map of the chamber.

DESCRIPTION OF EXAMPLES

Overview

In a cardiac procedure involving inserting a probe, comprising an insertion tube, into a heart chamber, it is useful to present to a physician performing the procedure a display of a graphical image of the distal part of the probe within the chamber. If the distal part comprises a basket assembly, such as may be used for a diagnostic and/or a therapeutic procedure, the graphical image may use an icon representing the assembly. However, during the procedure, the form of the assembly, herein assumed to comprise the shape and the orientation of the assembly, may change from an unconstrained form to a constrained form, for example if the assembly presses on a wall of the chamber, but the icon may not show the changes.

Embodiments of the disclosure provide a system for presenting the changed form of the basket assembly on a display. The basket assembly is assumed to comprise multiple resilient spines, connected at their proximal ends to a distal end of the insertion tube of the probe, and joined together at their distal ends to make the basket assembly. The spines typically distributed are symmetrically around a basket axis, the axis comprising a line from the spine distal ends to the spine proximal ends.

There is a force sensor at the insertion tube distal end and the sensor outputs a value of the force on the assembly. The measured force is resolved into a component parallel to the basket axis, herein termed an axial component, and a force orthogonal to the axis, herein termed an equatorial component. The axial component is assumed to alter the shape of the basket by compressing the unconstrained basket along the basket axis, to make a constrained form having a different form from that of the unconstrained basket. The equatorial component is assumed not to alter the shape of the basket, but rather to rotate the basket about the insertion tube distal end so that the orientation of the basket is changed. The compression is assumed to be linearly dependent on the value of the axial force component; the rotation is assumed to be linearly dependent on the value of the equatorial force component. The constants of proportionality for the two dependencies are different, and each may be measured prior to the use of the catheter in the procedure.

During the procedure, a processor may use the force measured by the force sensor, together with the two known constants of proportionality, to determine numerical values of the compression caused by the axial force component, and of the angle of rotation caused by the equatorial force component. The processor may then use the numerical values to render on a display of the basket assembly a representation showing the constrained form of the assembly.

System Description

In the following description, like elements are identified by the same numeral, and are differentiated, where required, by having a letter attached as a suffix to the numeral.

Figure 1:
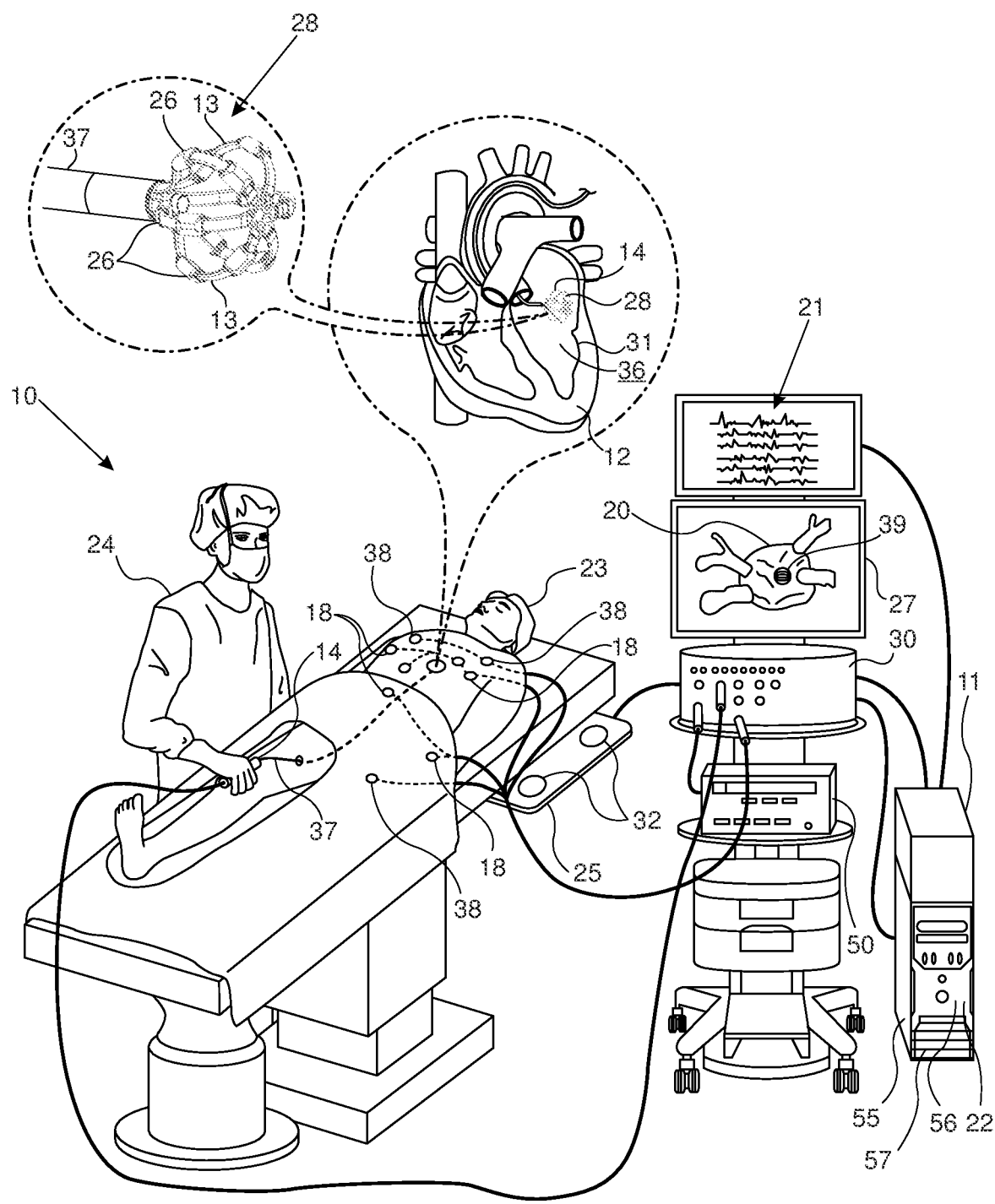
FIG. 1 shows a catheter-based electrophysiology mapping and ablation system being used for a medical procedure.

Reference is now made to FIG. 1 which shows a catheter-based electrophysiology mapping and ablation system 10 being used for a medical procedure. System 10 includes multiple catheters, which are percutaneously inserted by a physician 24 through the patient's vascular system into a chamber or vascular structure of a heart 12 of a patient 23. Typically, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. An example catheter 14, also referred to herein as probe 14, that is configured for ablation is illustrated herein, the probe comprising an insertion tube 37 and a distal section 28 fixed to a distal end of the tube. Physician 24 brings distal section 28 into contact with a heart wall 31 of a chamber 36 of heart 12, for the purpose of ablating a target site in the wall.

Figure 2:
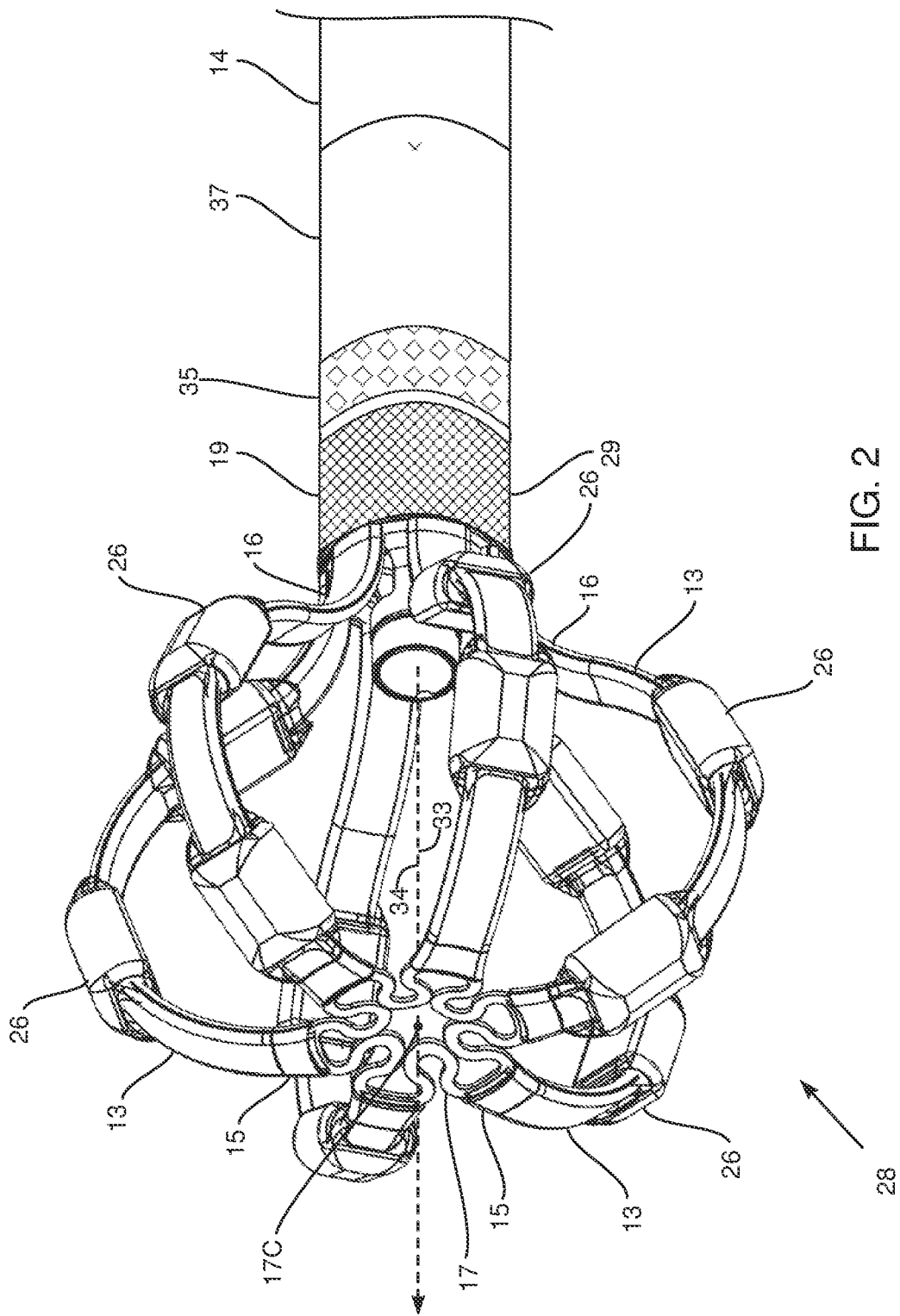
FIG. 2 is a schematic diagram of a distal section of a probe in an unconstrained form.

FIG. 2 is a schematic diagram of distal section 28 in an unconstrained form. In the description herein catheter 14 is assumed to comprise a basket catheter, so that distal section 28, also herein termed basket assembly 28 or just basket 28, is constructed as a plurality of resilient spines 13, each of the spines having at least one attached electrode 26 which may be used for ablation. Each spine 13 has a common length, and respective distal terminations 15 of the spines are connected to a connection 17. Respective proximal terminations 16 of the spines are fixedly located at, and exit from, a distal end 19 of tube 37. Catheter 14 additionally includes a force sensor 29 located at distal end 19. Sensor 29 is configured to generate signals indicating both the magnitude and the direction of the force on distal end 19. For one embodiment, a sensor similar to sensor 29 is described in U.S. Pat. No. 10,688,278.

In the example of basket 28 illustrated in FIG. 2 there are six spines 13 distributed symmetrically about a line between connection 17 and distal end 19, but it will be understood that basket 28 may have more or less than six symmetrically distributed spines.

In some embodiments a position sensor 35 is also located in end 19. Alternatively or additionally, one or more such sensors may be incorporated into one or more of spines 13. Typically, position sensor 35 is a magnetic based position sensor including three magnetic coils for sensing three-dimensional (3D) location and orientation of end 19.

Magnetic based position sensor 35 may be operated together with a location pad 25 including a plurality of magnetic coils 32 configured to generate magnetic fields in a predefined working volume. The real time position of sensor 35 may be tracked based on magnetic fields generated with location pad 25 and sensed by the sensor. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

As stated above, spine distal terminations 15 are connected to connection 17. The connection is configured so that in an unconstrained state of basket 28, e.g., when the basket is not in contact with any objects except air or blood, the spines are in a first predefined spine shape, and are connected to connection 17 to form basket 28 that defines a first predefined basket shape. In the following description, except as stated otherwise herein, the first predefined spine shape is assumed to be an arc of a circle, and the spines are connected to form basket 28 so that they lie on a sphere. Thus, the first predefined basket shape is a sphere, and it will be understood that a volume enclosed by spines 13 is approximately spherical.

In the unconstrained state of basket 28, the force registered by force sensor 29 is approximately zero. In one embodiment the spherical volume has a radius approximately equal to 6 mm. In the unconstrained state spines 13 are symmetrically arranged around a central axis 33 of the basket, the axis comprising a line from a center of proximal terminations 16 to a center 17C of connection 17. It will be understood that axis 33 is a rotational axis of symmetry, and that in the unconstrained state of basket 28 axis 33 is collinear with a rotational axis of symmetry 34 of distal end 19.

It will be appreciated that the unconstrained state of basket 28, illustrated in FIG. 2, exists before the basket enters the delivery sheath referred to above, as well as after the basket exits from the sheath and enters into the heart chamber. While in the sheath, basket 28 is constrained into a collapsed state by the walls of the sheath.

When in the heart chamber, basket 28 may also be constrained when it contacts walls of the chamber, the contact causing the walls to exert a force on the basket. The force due to the contact typically causes deformation of the basket, and/or displacement of the basket with respect to axis of symmetry 34 of distal end 19. Both the deformation and displacement are analyzed below, with regards to FIGS. 3-6.

Returning to FIG. 1, system 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182.

A recorder 11 displays electrograms 21 captured with body surface ECG electrodes 18 and intracardiac electrograms (IEGM) that may be captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes 26. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

A patient interface unit (PIU) 30 is an interface configured to establish electrical communication between catheters, electrophysiological equipment, a power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, a processor 22 with memory or storage with appropriate operating software loaded therein, and user interface capability. Processor 22 operates system 10. Workstation 55 may provide multiple functions, optionally including (1) modeling the endocardial anatomy in three-dimensions (3D) and rendering a model or anatomical map 20 of heart 12 or a portion thereof for display on a display device 27, (2) displaying on display device 27 activation sequences (or other data) compiled from recorded electrograms 21 in representative visual indicia or imagery superimposed on the rendered anatomical map 20, (3) displaying a representation 39, incorporating real-time location and orientation values, of basket 28 within heart chamber 36, and (4) displaying on display device 27 sites of interest such as places where ablation energy has been applied. One commercial product embodying elements of the system 10 is available as the CARTO™ 3 System, available from Biosense Webster, Inc., 31 Technology Drive, Suite 200, Irvine, CA 92618.

In embodiments of the disclosure, the real-time display of the position of basket 28 referred to above takes into account any deformation in the basket form from its unconstrained state, by modeling the deformation. In addition, the modeling provides location data for electrodes 26 of basket 28.

Figure 3:
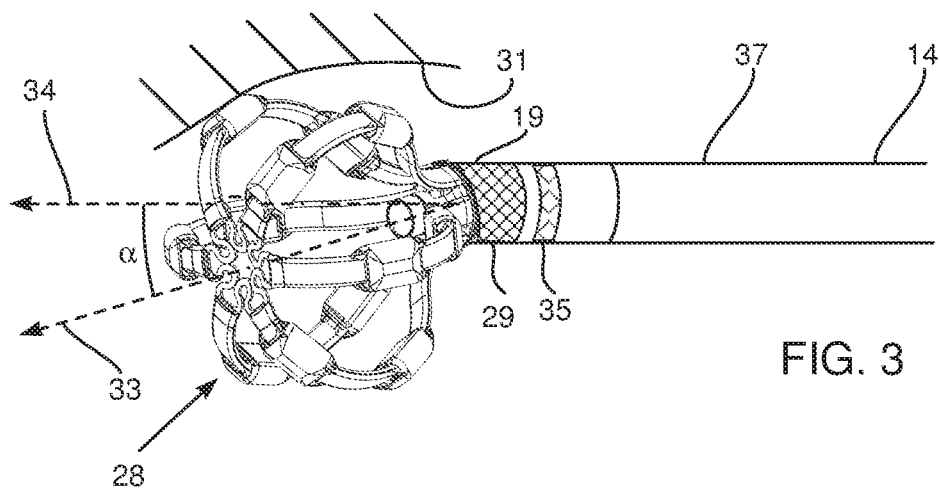
FIG. 3 is a schematic diagram illustrating a basket assembly when it is in a chamber of a heart.

FIG. 3 is a schematic diagram illustrating basket 28 when it is in chamber 36 of heart 12, and when it is contacting wall 31 of the chamber. The contact may typically constrain the basket, by deflecting the whole basket so that central axis 33 of symmetry of the basket is no longer collinear with rotational axis 34 of symmetry of distal end 19. Thus, in the constrained deflected state there is a non-zero angle α between the two axes of symmetry. In this type of basket constraint, the first predefined basket shape and the first predefined spine shape are unchanged, but the position and/or the orientation of the whole basket changes.

The contact may typically also constrain the basket by compressing it along its central axis 33 of symmetry. In this type of constraint, spines 13, which in the unconstrained state of the basket are in the form of arcs of a circle (since the basket spines enclose a spherical volume), are assumed to be deformed to sections of ellipses. By symmetry considerations, it will be understood that in the constrained state the compression along axis 33 deforms basket 28 to enclose an ellipsoid of revolution around axis 33.

As stated above, force sensor 29 generates signals that enable processor 22 to formulate the force, in magnitude and direction, on the sensor, and consequently on basket 28. For clarity, in the following description of the effect of the force, catheter 14 is assumed to define a set of Cartesian xyz axes, where the z-axis corresponds to rotational axis of symmetry 34 of the distal end of the catheter, and the x and y axes are orthogonal axes in a plane orthogonal to the z-axis.

Figure 4:
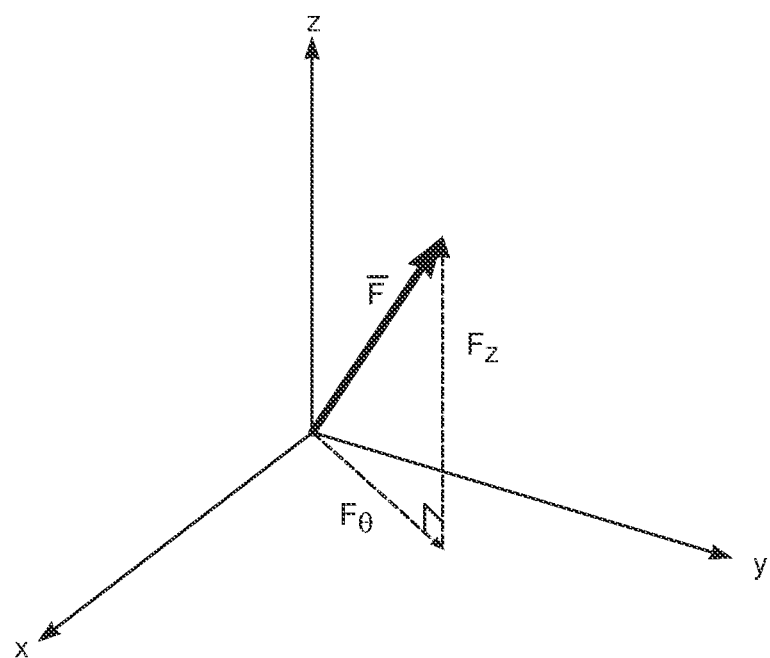
FIG. 4 illustrates how embodiments of the disclosure analyze a force determined by a processor.

FIG. 4 illustrates how embodiments of the disclosure analyze the force determined by processor 22. As illustrated in the figure, the processor resolves a vector force F into two orthogonal components: a force $F_z$ parallel to the z-axis, i.e., parallel to axis 34, and a force $F_\theta$ in the plane normal to the z-axis. Force $F_z$ is also herein termed an axial force; force $F_\theta$ is also herein termed an equatorial force.

The processor applies the values of each resolved force to a model of basket 28 to generate a constrained form of the basket, and from the constrained form determines positions of spines 13 of the basket in its constrained form. In generating the constrained form the processor assumes that for each of the resolved forces there is a linear relationship with the deformation caused by the resolved force, as illustrated by equations (1) and (2) below.

In response to axial force $F_z$, the basket is assumed to operate as a spring, according to equation (1):

$$\delta = \frac{F_z}{k_a} \quad (1)$$

where $\delta$ is an axial deformation to basket 28 caused by force $F_z$, and $k_a$ is an axial spring constant for the basket for this type of deformation. $\delta$, which is a distance measured in the z-axis direction, is illustrated and explained further with respect to FIG. 5.

As is also explained below, a value of $k_a$ for basket 28 is determined before being used for the procedure illustrated in FIG. 1.

In response to equatorial force Fe, the basket is assumed to rotate around distal end 29 of tube 37, the distal end operating as a spring-loaded ball joint according to equation (2):

$$\alpha = k_\theta \cdot F_\theta \quad (2)$$

where $\alpha$ is an angle of rotation of basket 28 caused by force $F_\theta$, and $k_\theta$ is a coefficient of stiffness for the basket for this type of deformation. $\alpha$, which is the angle of rotation from the z-axis direction, is illustrated and explained further with respect to FIG. 6.

As is also explained below, a value of $k_\theta$ for basket 28 is determined before being used for the procedure illustrated in FIG. 1.

Figure 5:
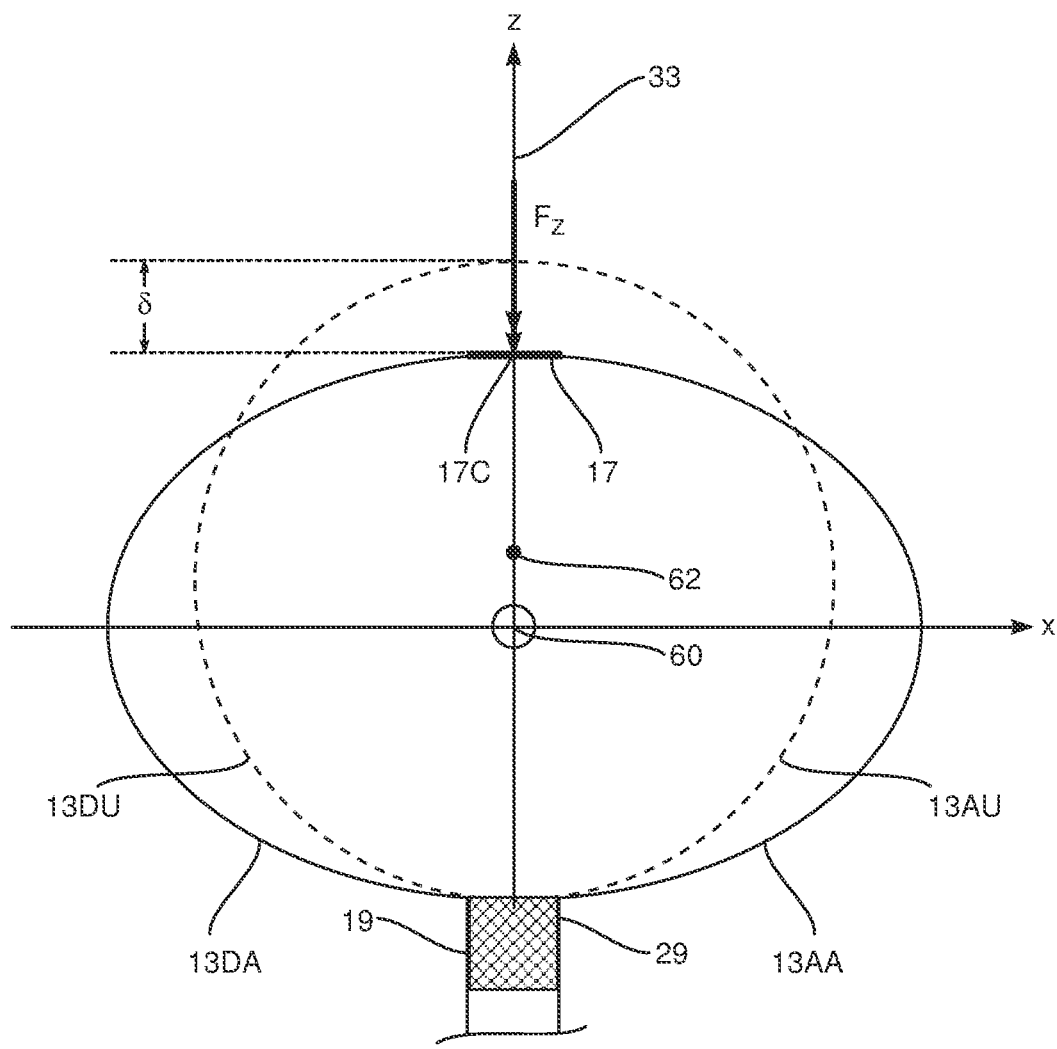
FIG. 5 illustrates how a resolved axial force is applied to an unconstrained model of a basket assembly.

FIG. 5 illustrates how the resolved axial force $F_z$ is applied to an unconstrained model of basket 28. As stated above, basket 28 has six spines 13 distributed symmetrically, comprising spines 13A, 13B, . . . 13E, 13F, and the figure shows a pair of spines 13A, 13D, connected together to connection 17 to lie, in the unconstrained state of the basket, on a circle. The figure also shows spines 13A, 13D in their constrained state due to an axial force, along axis 33, and to distinguish the states in the figure spines 13A, 13D are respectively labelled 13AU, 13DU for the unconstrained case, and 13AA, 13DA for the constrained state.

For clarity, the spines have been drawn on a set of Cartesian xz axes, where the z-axis is collinear with rotational axis of symmetry 34, and the x-axis is orthogonal to the z-axis and is in the plane defined by connected spines 13A and 13D. The position of the x-axis has been set so that an origin of the two axes corresponds to a center 60 of an ellipse formed by spines 13A, 13D when constrained, as is explained further below.

As explained above, spines 13 in their unconstrained state are assumed to form part of a sphere, so that spines 13AU, 13DU lie on a circle, which is assumed to have a radius "a" and a center a point 62. An equation for the circle, disregarding a translation of the center of the circle from the origin along the z-axis, is:

$$x^2 + z^2 = a^2 \quad (3)$$

The constraint of axial force $F_z$ is assumed to deform spines 13A, 13D to spines 13AA, 13DA, and the deformed spines are assumed to lie on an ellipse. The deformation is assumed to translate connection 17, the meeting place of the distal ends of spines 13A and 13D, by a distance $\delta$, along the z-axis. Distance $\delta$ is a linear metric.

Thus a minor axis of the ellipse, the line segment between connection 17 and the proximal connections of spines 13DA and 13AA at distal end 19, has a length ($2a-\delta$), and a length of the semi-minor axis of the ellipse is:

$$\left(\frac{2a-\delta}{2}\right) \equiv \left(a - \frac{\delta}{2}\right) \quad (4)$$

The deformation into an ellipse is assumed to form the major axis of the ellipse by extending the unconstrained spines by approximately $\delta$ on each side of the z-axis, so that the major axis has a length ($2a+2\delta$). Thus a length of the semi-major axis of the ellipse is:

$$\left(\frac{2a+\delta}{2}\right) \equiv (a + \delta) \quad (5)$$

From expressions (4) and (5) an equation for the ellipse formed by constrained spines 13DA and 13AA is:

$$\frac{x^2}{(a+\delta)^2} + \frac{z^2}{\left(a - \frac{\delta}{2}\right)^2} = 1 \quad (6)$$

Equations (3) and (6) respectively correspond to the shapes of spines 13A and 13D in their unconstrained and constrained forms, when the spines are constrained by axial force $F_z$. Thus, processor 22 is able to use equation (6) to calculate the positions of spines 13A, 13D in their constrained form.

The other spines of basket 28, when the basket is constrained by axial force $F_z$, obey substantially similar equations to those of equations (3) and (6), since the basket is initially spherical and deforms to an ellipsoid of revolution about the basket axis of symmetry 33. Thus, while for simplicity equations (3) and (6) have been written for a two-dimensional (2D) system, those having ordinary skill in the art will be able to adapt the equations for the three-dimensional (3D) basket 28.

In addition, it will be understood that the spherical and ellipsoidal shapes referred to above are by way of example, and one of ordinary skill in the art will be aware of other initial shapes for basket 28, and corresponding shapes for the basket when constrained by an axial force $F_z$. Both the unconstrained and the constrained shape are topologically equivalent to a spherical shape. For example the unconstrained shape may be ellipsoidal, and the constrained shape may be a different ellipsoidal shape, or even a spherical shape.

Thus, for a 3D system equations (3) and (6) may be generalized to:

$$\{(x,y,z)|f(x,y,z)\} \tag{7}$$

where the function f(x, y, z) describes the predefined shape of the unconstrained basket, and $$\{(x,y,z)|g(x,y,z,\delta)\} \tag{8}$$

where the function g(x, y, z, δ) describes the predefined shape of the constrained basket when the unconstrained basket has been compressed a distance δ.

In the procedure illustrated in FIG. 1, processor 22 may use equations (7) and (8) to calculate the change of shape of basket 28 when it is constrained by a force having an axial component $F_z$.

Figure 6:
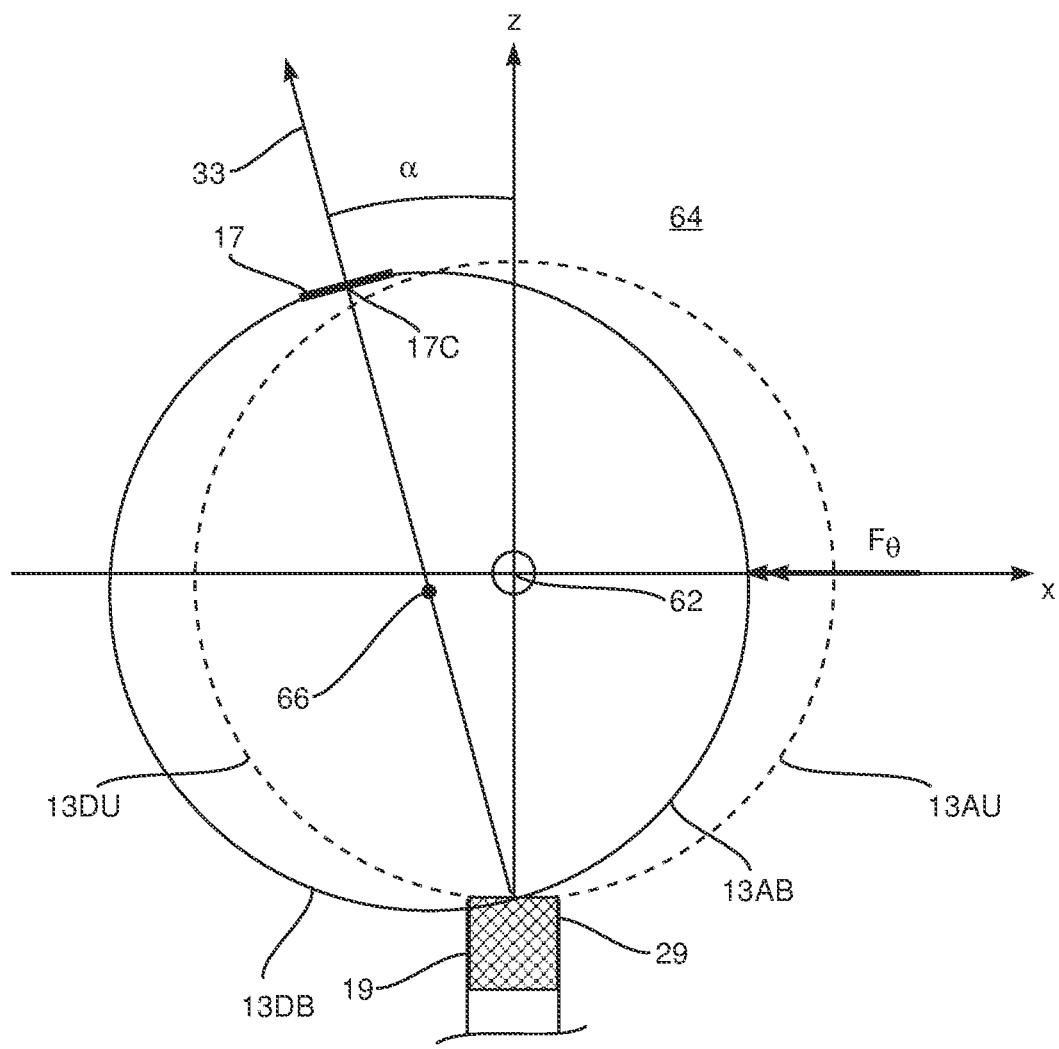
FIG. 6 illustrates how a resolved equatorial force is applied to an unconstrained model of a basket assembly.

FIG. 6 illustrates how the resolved equatorial force Fe is applied to an unconstrained model of basket 28. In FIG. 6 the x-axis, which passes through center 62 of the unconstrained basket 28, has been drawn to lie in a plane 64 defined by equatorial force Fe and the z-axis. (The z-axis corresponds to axis of symmetry 33 of basket 28 before the action of force Fe.)

In contrast to the effect of axial force $F_z$, the equatorial force $F_\theta$ is assumed not to deform the spines of the basket, so that the shape of the spines, and of the basket, is unchanged. Rather, as stated above, equatorial force $F_\theta$ is assumed to rotate the basket, in an undeformed state, about an axis orthogonal to plane 64 and passing through distal end 29 of probe 14. The rotation assumes that distal end 29 behaves as a spring-loaded ball joint according to equation (2).

FIG. 6 has been drawn illustrating the same unconstrained spines 13AU, 13DU, as FIG. 5, and the rotated spines for the case shown in FIG. 6 are labelled 13AB, 13DB.

The rotation of basket 28 translates center point 62 to a center point 66 of the rotated basket. Thus, for a rotation of α, the 2D coordinates of point 66 are:

$$(x, z) = ((-a\sin\alpha), (a\cos\alpha - a)) \tag{9}$$

and an equation for the rotated spines 13AB, 13DB is:

$$(x + a\sin\alpha)^2 + (z - (a\cos\alpha - a))^2 = a^2 \tag{10}$$

Once the location of the translated center point has been established as in equation (9), since basket 28 has not been deformed, processor 22 is able to use the new center location to evaluate the locations of all spines of the basket.

Equation (3), reproduced here, corresponds to the circle of spines 13AU, 13DU when the spines are unconstrained by equatorial force $F_\theta$.

$$x^2 + z^2 = a^2 \tag{3}$$

Equations (3) and (10) respectively correspond to the shapes of spines 13A and 13D in their unconstrained and constrained forms, when the spines are constrained by equatorial force $F_\theta$. Thus, processor 22 is able to use equation (10) to calculate the positions of spines 13A, 13D in their constrained form.

In addition, when all the spines of basket 28 are constrained by equatorial force Fe processor 22 is able to use the center of the basket, as given by equation (9), to determine the locations of all of the spines of the basket when the basket is constrained by equatorial force $F_\theta$.

Equation (3) has been generalized to 3D equation (7), reproduced here:

$$\{(x,y,z)|f(x,y,z)\} \tag{7}$$

where the function f(x, y, z) describes the predefined shape of the unconstrained basket, Similarly, equation (10) may be generalized to a 3D equation:

$$\{(x,y,z)|g(x,y,z,\alpha)\} \tag{8}$$

where the function f(x, y, z, α) describes the basket as having the same shape as is given by equation (7), but rotated by an angle α.

In the procedure illustrated in FIG. 1, processor 22 may use equations (7) and (11) to calculate the change of orientation of basket 28 when it is constrained by a force having an equatorial component $F_\theta$.

The description above explains how processor 22 may evaluate changes in the form of basket assembly 28 due to an axial force component of force F̄ and, separately, due to an equatorial force component of force F̄. The processor uses equations (7) and (8) to evaluate the axial component change, and equations (7) and (11) for the equatorial component change.

To determine the change in form of basket assembly 28 during a procedure, where the axial and equatorial components are simultaneously active, the processor may apply the results of the equations sequentially. E.g., initially determine the shape change using equations (7) and (8), and then use the result of the shape change (equation (8)) as the expression describing the initial state of the basket assembly when determining the orientation change. It will be understood that both the shape change and the orientation change may be expressed by numerical values.

Once processor 22 has determined the change in form of basket assembly 28 numerically, it may use these numerical values to render on display device 27 representation 39 showing the constrained form of the assembly. As illustrated in FIG. 1, representation 39 is typically incorporated into anatomical map 20.

The description above assumes that a pair of spines of basket assembly 28 may be selected to lie on a 2D curve, such as a circle for the example analyzed above. This is possible for any number of spines in a basket assembly such as assembly 28. In the case where there is an odd number of spines, the calculations previously disclosed can be done for each spine, rather than a pair of spines, while having a mirrored spine for purposes of calculation. Representation 39 may then display the spines without their mirrored spine. It will be understood that the spine distribution does not need to be rotationally symmetric as long as $k_\theta$ is known with respect to where on the xy plane $F_\theta$ falls. Thus, those having ordinary skill in the art will be able to modify the description, mutatis mutandis, for basket assemblies where the spines are not distributed symmetrically, and/or where there are uneven numbers of spines.

As described above, each spine 13 has at least one electrode 26 attached to the spine, and it will be understood that these electrodes are in known positions on their respective spines when basket assembly is in its unconstrained state. For a constrained state of the assembly, processor 22 may use the initial electrode positions and the new locations of the spines of the basket in its constrained state, to calculate new positions for the electrodes for the constrained state.

Figure 7:
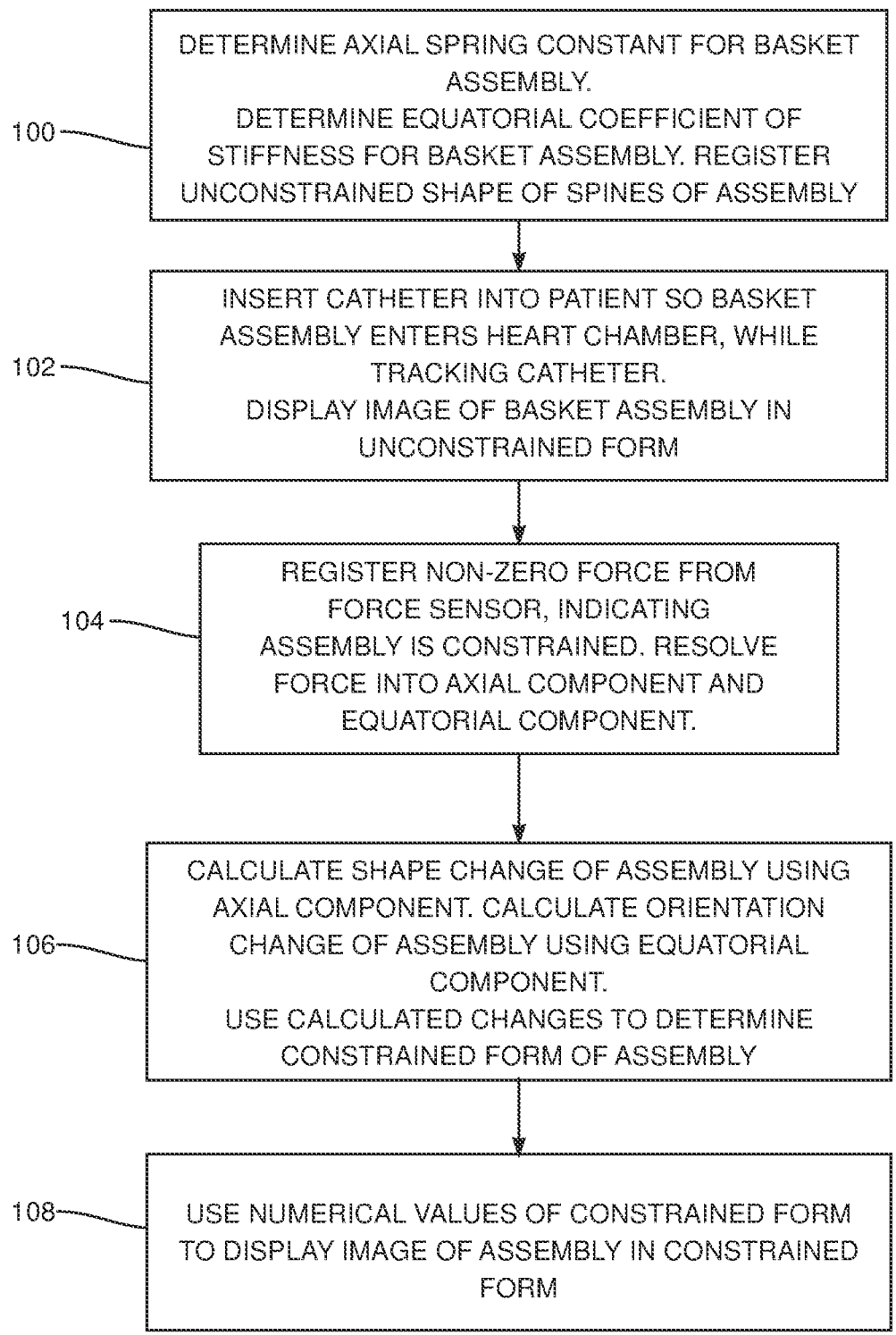
FIG. 7 is a flowchart of steps taken by a processor in rendering an image of a basket assembly, when it is in its constrained form, to a display device.

FIG. 7 is a flowchart of steps taken by processor 22 in rendering an image of basket assembly 28, when it is in its constrained form, to display device 27. The image may be generated during the procedure illustrated in FIG. 1.

In an initial step 100, typically performed prior to initiation of the procedure, the processor is provided with the axial spring constant $k_a$ of assembly 28 defined in equation (1), and with the assembly coefficient of stiffness $k_\theta$ defined in equation (2). The values may be determined experimentally, by applying known axial and equatorial forces to the assembly and measuring the respective changes of shape and of orientation. In one embodiment $k_a = -31.86$ g/mm (the negative sign is indicative of the opposing directions of $\delta$ and $F_z$) and $k_\theta = 0.29$ degrees/g, but the values of $k_a$ and $k_\theta$ may be larger or smaller than these values.

In addition, in the initial step, the processor is provided with numerical values, and/or equations, describing the shape of basket assembly 28, i.e., the shape of each spine 13, when the assembly is in its unconstrained state.

In a catheter insertion step 102, physician 24 inserts catheter 14 into patient 23 so that assembly 28 enters heart chamber 36. The processor tracks assembly 28 in both location and orientation, using position sensor 35, and registers the output of force sensor 29. For the tracked location and orientation, in the cases when the force registered by force sensor 29 is approximately zero, the processor displays an image of the basket assembly on display device 27 in its unconstrained form.

In a continuing insertion step 104, while the processor is still tracking the location and orientation of the assembly, the processor registers that the output from force sensor 29 indicates there is a non-zero force acting on the sensor, and thus on the basket assembly. Using the tracked orientation of the assembly, the processor resolves the force indicated by the sensor output into an axial component and an equatorial component.

In a calculation step 106, the processor uses the force components to calculate a shape change of assembly 28 and an orientation change of the assembly, as described above with reference to FIGS. 5 and 6. The processor uses the calculated changes to determine a constrained form for each of the splines of the assembly, so as to find the shape and the orientation of the basket as it is constrained by the force registered by the force sensor. As is also described above, the processor may also calculate positions of electrodes 26 on the constrained spines.

In an imaging step 108, processor 22 uses numerical values of the constrained form to calculate an image of the constrained form of the basket assembly, and to render the image to display device 27 as a representation of the constrained form. The representation is exemplified by representation 39 in FIG. 1.

Examples

Example 1. Apparatus for medical treatment, comprising:
a probe, comprising:
an insertion tube having a distal end configured for insertion into a body cavity of a living subject;
a basket assembly comprising multiple resilient spines coupled to the distal end of the insertion tube and joined together in a predefined form when the basket assembly is unconstrained by external forces; and
a force sensor configured to output an indication of a force exerted on the basket assembly within the body cavity; and
a processor, configured to receive the indication of the force, to compute a constrained form of the basket assembly, different from the predefined form, responsively to the force, and to render to a display a graphical image representing the constrained form of the basket assembly.

Example 2. The apparatus according to example 1, wherein the multiple spines have spine distal ends that are joined to a connection having a central point, and spine proximal ends fixed to the insertion tube distal end, thereby defining an assembly axis between the central point and the insertion tube distal end, and wherein the processor is configured to resolve the force into an axial component parallel to the assembly axis, and an equatorial component orthogonal to the assembly axis, and to compute the constrained form responsively to at least one of the axial component and the equatorial component Example 3. The apparatus according to example 2, wherein the predefined form has a predefined shape, and wherein the constrained form computed responsively to the axial component comprises a constrained shape different from the predefined shape.

Example 4. The apparatus according to example 3, wherein the constrained shape differs from the predefined shape by a linear metric parallel to the assembly axis.

Example 5. The apparatus according to example 4, wherein the linear metric is directly proportional to the axial component.

Example 6. The apparatus according to example 2, wherein the predefined form has a predefined orientation, and wherein the constrained form computed responsively to the equatorial component comprises a constrained orientation different from the predefined orientation.

Example 7. The apparatus according to example 6, wherein the constrained orientation differs from the predefined orientation by an angle measured about a rotation axis orthogonal to the assembly axis.

Example 8. The apparatus according to example 7, wherein the angle is directly proportional to the equatorial component.

Example 9. The apparatus according to example 7, wherein the rotation axis passes through the insertion tube distal end and is orthogonal to the equatorial component.

Example 10. The apparatus according to example 1, wherein the force sensor is fixedly located at the distal end of the insertion tube.

Example 11. The apparatus according to example 1, wherein a given spine of the multiple spines has an electrode fixedly attached thereto at a predefined position thereon, and wherein the processor is configured to calculate a constrained position on the given spine of the electrode, different from the predefined position, responsively to computing the constrained form of the basket assembly.

Example 12. The apparatus according to example 1, wherein the predefined form and the constrained form respectively comprise a predefined shape and a constrained shape, and wherein the predefined shape and the constrained shape are each topologically equivalent to a spherical shape.

Example 13. A method for medical treatment, comprising:
providing a probe, comprising:
an insertion tube having a distal end configured for insertion into a body cavity of a living subject;
a basket assembly comprising multiple resilient spines coupled to the distal end of the insertion tube and joined together in a predefined form when the basket assembly is unconstrained by external forces; and
a force sensor configured to output an indication of a force exerted on the basket assembly within the body cavity;
receiving the indication of the force;
computing a constrained form of the basket assembly, different from the predefined form, responsively to the force; and
rendering to a display a graphical image representing the constrained form of the basket assembly.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for medical treatment, comprising:
a probe, comprising:
an insertion tube having a distal end configured for insertion into a body cavity of a living subject;
a basket assembly comprising multiple resilient spines coupled to the distal end of the insertion tube and joined together in a predefined form when the basket assembly is unconstrained by external forces; and
a force sensor configured to output an indication of a force exerted on the basket assembly upon physical contact of some of the spines on an external member; and
a processor, configured to receive the indication of the force, to compute a constrained form of the basket assembly, different from the predefined form, responsively to the force, and to render to a display a graphical image representing the constrained form of the basket assembly.

2. The apparatus according to claim 1, wherein the multiple spines have spine distal ends that are joined to a connection having a central point, and spine proximal ends fixed to the insertion tube distal end, thereby defining an assembly axis between the central point and the insertion tube distal end, and wherein the processor is configured to resolve the force into an axial component parallel to the assembly axis, and an equatorial component orthogonal to the assembly axis, and to compute the constrained form responsively to at least one of the axial component and the equatorial component.

3. The apparatus according to claim 2, wherein the predefined form has a predefined shape, and wherein the constrained form computed responsively to the axial component comprises a constrained shape different from the predefined shape.

4. The apparatus according to claim 3, wherein the constrained shape differs from the predefined shape by a linear metric parallel to the assembly axis.

5. The apparatus according to claim 4, wherein the linear metric is directly proportional to the axial component.

6. The apparatus according to claim 2, wherein the predefined form has a predefined orientation, and wherein the constrained form computed responsively to the equatorial component comprises a constrained orientation different from the predefined orientation.

7. The apparatus according to claim 6, wherein the constrained orientation differs from the predefined orientation by an angle measured about a rotation axis orthogonal to the assembly axis.

8. The apparatus according to claim 7, wherein the angle is directly proportional to the equatorial component.

9. The apparatus according to claim 7, wherein the rotation axis passes through the insertion tube distal end and is orthogonal to the equatorial component.

10. The apparatus according to claim 1, wherein the force sensor is fixedly located at the distal end of the insertion tube.

11. The apparatus according to claim 1, wherein a given spine of the multiple spines has an electrode fixedly attached thereto at a predefined position thereon, and wherein the processor is configured to calculate a constrained position on the given spine of the electrode, different from the predefined position, responsively to computing the constrained form of the basket assembly.

12. The apparatus according to claim 1, wherein the predefined form and the constrained form respectively comprise a predefined shape and a constrained shape, and wherein the predefined shape and the constrained shape are each topologically equivalent to a spherical shape.

13. A method for medical treatment, comprising:
providing a probe, comprising:
an insertion tube having a distal end;
a basket assembly comprising multiple resilient spines coupled to the distal end of the insertion tube and joined together in a predefined form when the basket assembly is unconstrained by external forces; and
a force sensor configured to output an indication of a force exerted on the basket assembly by physical contact of some of the spines on a member;
receiving the indication of the force;
computing a constrained form of the basket assembly, different from the predefined form, responsively to the force; and
rendering to a display a graphical image representing the constrained form of the basket assembly.

14. The method according to claim 13, wherein the multiple spines have spine distal ends that are joined to a connection having a central point, and spine proximal ends fixed to the insertion tube distal end, thereby defining an assembly axis between the central point and the insertion tube distal end, the method comprising resolving the force into an axial component parallel to the assembly axis, and an equatorial component orthogonal to the assembly axis, and computing the constrained form responsively to at least one of the axial component and the equatorial component.

15. The method according to claim 14, wherein the predefined form has a predefined shape, and wherein the constrained form computed responsively to the axial component comprises a constrained shape different from the predefined shape.

16. The method according to claim 15, wherein the constrained shape differs from the predefined shape by a linear metric parallel to the assembly axis.

17. The method according to claim 16, wherein the linear metric is directly proportional to the axial component.

18. The method according to claim 14, wherein the predefined form has a predefined orientation, and wherein the constrained form computed responsively to the equatorial component comprises a constrained orientation different from the predefined orientation.

19. The method according to claim 18, wherein the constrained orientation differs from the predefined orientation by an angle measured about a rotation axis orthogonal to the assembly axis.

20. The method according to claim 19, wherein the angle is directly proportional to the equatorial component.

21. The method according to claim 19, wherein the rotation axis passes through the insertion tube distal end and is orthogonal to the equatorial component.

22. The method according to claim 13, wherein the force sensor is fixedly located at the distal end of the insertion tube.

23. The method according to claim 13, wherein a given spine of the multiple spines has an electrode fixedly attached thereto at a predefined position thereon, the method further comprising calculating a constrained position on the given spine of the electrode, different from the predefined position, responsively to computing the constrained form of the basket assembly.

24. The method according to claim 13, wherein the predefined form and the constrained form respectively comprise a predefined shape and a constrained shape, and wherein the predefined shape and the constrained shape are each topologically equivalent to a spherical shape.

* * * * *